(12) United States Patent
Batista et al.

(10) Patent No.: US 12,144,378 B2
(45) Date of Patent: Nov. 19, 2024

(54) AEROSOL-GENERATING DEVICE COMPRISING SINGLE USE MOUTHPIECE

(71) Applicant: PHILIP MORRIS PRODUCTS S.A., Neuchatel (CH)

(72) Inventors: Rui Nuno Batista, Morges (CH); Andreas Lob, Rhein (DE)

(73) Assignee: Philip Morris Products S.A., Neuchatel (CH)

( * ) Notice: Subject to any disclaimer, the term of this patent is extended or adjusted under 35 U.S.C. 154(b) by 505 days.

(21) Appl. No.: 17/619,001

(22) PCT Filed: Jun. 26, 2020

(86) PCT No.: PCT/EP2020/068072
§ 371 (c)(1),
(2) Date: Dec. 14, 2021

(87) PCT Pub. No.: WO2020/260613
PCT Pub. Date: Dec. 30, 2020

(65) Prior Publication Data
US 2022/0295898 A1 Sep. 22, 2022

(30) Foreign Application Priority Data
Jun. 28, 2019 (EP) .................................. 19183204

(51) Int. Cl.
*A24F 7/02* (2006.01)
*A24F 40/485* (2020.01)

(52) U.S. Cl.
CPC .............. *A24F 40/485* (2020.01); *A24F 7/02* (2013.01)

(58) Field of Classification Search
None
See application file for complete search history.

(56) References Cited

U.S. PATENT DOCUMENTS

| | | |
|---|---|---|
| 5,133,368 A | 7/1992 | Neumann |
| 5,246,422 A | 9/1993 | Favre |
| 5,799,663 A | 9/1998 | Gross |

(Continued)

FOREIGN PATENT DOCUMENTS

| | | |
|---|---|---|
| CN | 1285761 | 2/2001 |
| EP | 3298911 | 3/2018 |

(Continued)

OTHER PUBLICATIONS

Office Action issued in Japan for Application No. 2021-576998 dated Dec. 12, 2022 (5 pages). English translation included.

(Continued)

*Primary Examiner* — Philip Y Louie
*Assistant Examiner* — Eric M Fierce
(74) *Attorney, Agent, or Firm* — Mueting Raasch Group

(57) ABSTRACT

The invention relates to an aerosol-generating device. The device may comprise a main body (10) that may comprise a connection portion (16). The device may further comprise a removable mouthpiece (12) that may comprise a first connection element (14). The first connection element may be configured removably engageable with the connection portion of the main body. The first connection element may be configured to irreversibly change upon disengagement of the first connection element from the connection portion of the main body.

13 Claims, 4 Drawing Sheets

(56) References Cited

U.S. PATENT DOCUMENTS

| | | |
|---|---|---|
| 7,631,782 B2 | 12/2009 | Engelbrecht |
| 8,584,668 B2 | 11/2013 | Hodson |
| 9,949,508 B2 | 4/2018 | Chang |
| 9,980,522 B1 | 5/2018 | Heidl |
| 10,206,428 B2 | 2/2019 | Thorens |
| 11,641,878 B2 | 5/2023 | Li |
| 2004/0139967 A1* | 7/2004 | Hodson ............ A61M 15/0025 128/200.23 |
| 2006/0213505 A1 | 9/2006 | Hodson |
| 2009/0235939 A1 | 9/2009 | Gonsalves |
| 2012/0305009 A1 | 12/2012 | Morgan |
| 2013/0074857 A1 | 3/2013 | Buchberger |
| 2013/0167850 A1 | 7/2013 | Al-Aawar |
| 2016/0338412 A1 | 11/2016 | Monsees |
| 2018/0235277 A1 | 8/2018 | Lin |
| 2018/0279670 A1 | 10/2018 | Eckles |

FOREIGN PATENT DOCUMENTS

| | | |
|---|---|---|
| JP | H09-509845 | 9/1995 |
| JP | 2015-529082 | 10/2015 |
| RU | 2661840 | 7/2018 |
| SU | 1641183 | 4/1991 |
| WO | WO 99/25406 | 5/1999 |
| WO | WO 03/080149 | 10/2003 |
| WO | WO 2011/071897 | 6/2011 |
| WO | WO 2013/171206 | 11/2013 |
| WO | WO 2014/039308 | 3/2014 |
| WO | WO 2016/169796 | 10/2016 |
| WO | WO 2017/093721 | 6/2017 |
| WO | WO 2018/011037 | 1/2018 |
| WO | WO 2018/023087 | 2/2018 |
| WO | WO 2019/119650 | 6/2019 |

OTHER PUBLICATIONS

Office Action issued in China for Application No. 202080041934.3 dated Dec. 19, 2023 (14 pages).

Office Action issued in Russia for Application No. 2021135714 dated Apr. 19, 2022 (4 pages). English translation included.

PCT International Search Report and Written Opinion for PCT/EP2020/068072 dated Aug. 14, 2020 (16 pages).

* cited by examiner

AEROSOL-GENERATING DEVICE COMPRISING SINGLE USE MOUTHPIECE

This application is a U.S. National Stage Application of International Application No. PCT/EP2020/068072 filed Jun. 26, 2020, which was published in English on Dec. 30, 2020, as International Publication No. WO 2020/260613 A1. International Application No. PCT/EP2020/068072 claims priority to European Application No. 19183204.7 filed Jun. 28, 2019.

The present invention relates to an aerosol-generating device and to a single use mouthpiece for use with an aerosol-generating device.

It is known to provide an aerosol-generating device for generating an inhalable vapor. Such aerosol-generating devices may heat an aerosol-forming substrate without burning the aerosol-forming substrate. Such aerosol-forming substrates may be provided as part of an aerosol-generating article. Such aerosol-generating devices may be arranged to receive an aerosol-generating article comprising an aerosol-forming substrate. The aerosol-generating article may have a rod shape for insertion of the aerosol-generating article into a heating chamber of the aerosol-generating device. A heating element may be arranged in or around the heating chamber for heating the aerosol-forming substrate when the aerosol-generating article is received in the heating chamber of the aerosol-generating device. Typically, the aerosol-forming substrate is vaporized by the heating element and aerosol is subsequently formed. The aerosol-generating device may comprise a mouthpiece. A user may inhale the generated aerosol through the mouthpiece. The mouthpiece may be arranged at a proximal end of the heating chamber. During use, unwanted contaminants may agglomerate in the mouthpiece and negatively affect hygiene of the mouthpiece. Further, the mouthpiece may be configured to influence the generated aerosol, for example by providing aerosol-forming substrate in the mouthpiece. After the aerosol-forming substrate is depleted, the mouthpiece may no longer optimally influence the generated aerosol in a desired way.

It would be desirable to have an aerosol-generating device with enhanced hygiene. It would be desirable to have an aerosol-generating device with a replaceable mouthpiece. It would be desirable to have an aerosol-generating device in which a mouthpiece cannot be used or re-used multiple times. It would be desirable to have an aerosol-generating device with a single use mouthpiece. It would be desirable to have a mouthpiece with enhanced hygiene. It would be desirable to have a replaceable mouthpiece. It would be desirable to have a mouthpiece cannot be used or re-used multiple times. It would be desirable to have a single use mouthpiece for an aerosol-generating device.

According to embodiments of the invention, there is provided an aerosol-generating device. The device may comprise a main body that may comprise a connection portion. The device may further comprise a removable mouthpiece that may comprise a first connection element. The first connection element may be configured removably engageable with the connection portion of the main body. The first connection element may be configured to irreversibly change upon disengagement of the first connection element from the connection portion of the main body.

According to embodiments of the invention, there is provided an aerosol-generating device. The device comprises a main body that comprises a connection portion. The device further comprises a removable mouthpiece that comprises a first connection element. The first connection element is configured removably engageable with the connection portion of the main body. The first connection element is configured to irreversibly change upon disengagement of the first connection element from the connection portion of the main body.

By configuring the first connection element to irreversibly change upon disengagement of the first connection element from the connection portion, a re-engagement of the mouthpiece with the main body is prevented. By preventing a re-engagement of the mouthpiece, the mouthpiece is configured as a single use mouthpiece. Providing a single use mouthpiece may be beneficial from a manufacturing perspective. Hygiene is improved, since a new mouthpiece has to be provided. If the mouthpiece is provided with aerosol-forming substrate, as described in detail below, re-engagement of the mouthpiece containing depleted aerosol-forming substrate is prevented.

The term "removably engageable" may refer to an element being both engageable and disengageable with another element. The engagement may be reversible or repeatable. The term "removably engageable" may refer to the first connection element of the mouthpiece being engageable with the connection portion of the main body. In other words, the first connection element can be engaged with the connection portion. Additionally, the first connection element is configured disengageable from the connection portion. Thus, the first connection element can be disengaged from the connection portion.

The term "irreversibly change" may refer to a physical or structural change. The term "irreversibly change" may refer to a physical or structural change of the first connection element. The change may occur during disengagement of the first connection element and the connection portion. The change may occur after disengagement of the first connection element and the connection portion. The change may as a result of disengagement of the first connection element and the connection portion. This physical or structural change is preferably irreversible. The physical or structural change may be such that the first connection element of the mouthpiece can no longer be engaged with the connection portion. Consequently, the mouthpiece may no longer be engageable with the main body of an aerosol-generating device. The connection portion of the main body is preferably not irreversibly changed during disengagement of the first connection element from the connection portion. The physical or structural change may be such that the first connection element of the mouthpiece is destroyed, broken or damaged in some way. The connection portion preferably remains intact for engagement with a new mouthpiece.

The first connection element may comprise a weakened region. The weakened region may be configured to plastically deform. The weakened region may be configured to plastically deform during disengagement of the first connection element and the connection portion of the main body. The weakened region may be configured to plastically deform after disengagement of the first connection element and the connection portion of the main body. The weakened region may be configured to plastically deform as a result of disengagement of the first connection element and the connection portion of the main body. The weakened region may be configured to fracture. The weakened region may be configured to fracture during disengagement of the first connection element and the connection portion of the main body. The weakened region may be configured to fracture after disengagement of the first connection element and the connection portion of the main body. The weakened region may be configured to fracture as a result of disengagement of the first connection element and the connection portion of the main body.

The irreversible change of the first connection element may be the plastic deformation of the first connection element. The plastic deformation may be an irreversible deformation. The plastic deformation is preferably not an elastic deformation. During the plastic deformation, a part of the first connection element may plastically deform. Alternatively, the whole first connection element may plastically deform during the plastic deformation. The plastic deformation may be a bending of the first connection element.

The first connection element may comprise a base. The first connection element may be connected to the mouthpiece at the base. The plastic deformation may take place at the base. The first connection element may bend at the base during the plastic deformation.

The irreversible change of the first connection element may be the fracture of the first connection element. The fracture may be irreversible. The fracture may be a break or rupture of the first connection element. The fracture may be a break or rupture of a portion of the first connection element. The fracture may be a shearing off of the first connection element. The fracture may be a shearing off of a portion of the first connection element. The first connection element may fully or partially fracture. A partial fracturing of the first connection element may be combined with a plastic deformation of the first connection element. The first connection element may rupture at the base.

The weakened region may be a region weakened in comparison to the rest of the first connection element. The term "weakened" may refer to a mechanical weakness. The term "weakened" may refer to a structural weakness. The mechanical or structural weakness may be a mechanical or structural weakness in comparison to the rest of the first connection element. The weakened region may be susceptible to a plastic deformation or rupture as described above. The weakened region may be susceptible to a fracture. The weakened region may be susceptible to crack initiation or crack propagation.

Once the first connection element has been disengaged from the connection portion, the weakened region may be configured to prevent re-engagement between the first connection element and the connection portion of the main body to re-connect the mouthpiece to the main body.

The re-engagement may be prevented by the physical or structural change of the first connection element. Preferably, the physical or structural change modifies the first connection element such that the first connection element is no longer engageable with the connection portion of the main body.

The mouthpiece may comprise an airflow channel and an aerosol-forming substrate at least partially lining a surface of the airflow channel.

The airflow channel may be a central airflow channel. The airflow channel may be a hollow airflow channel. The airflow channel may run along the longitudinal axis of the aerosol-generating device. The airflow channel may run along the longitudinal axis of the mouthpiece. The airflow channel may run along the longitudinal axis of the main body. When the mouthpiece is engaged with the main body, the airflow channel of the mouthpiece may be fluidly connected to the airflow channel of the main body.

The aerosol-forming substrate may influence the aerosol generated by the aerosol-generating device. The aerosol-forming substrate may influence the flavour of the aerosol generated by the aerosol-generating device. Due to the mouthpiece preferably being configured as a single use mouthpiece, the mouthpiece may be removed from the main body when the aerosol-forming substrate is depleted. Subsequently, a new mouthpiece with fresh aerosol-forming substrate may be attached to the main body.

The aerosol-forming substrate may be viscous. The aerosol-forming substrate may be provided as a gel or slurry or paste. The aerosol-forming substrate may be provided in a carrier material as described in more detail below. The carrier material may be a capillary material. The carrier material may comprise a cellulose material. The aerosol-forming substrate may be a liquid provided in a carrier material.

The aerosol-forming substrate may line the airflow channel of the mouthpiece. The aerosol-forming substrate may be arranged inside the mouthpiece. The aerosol-forming substrate may line the entire airflow channel of the mouthpiece. The aerosol-forming substrate may partially line the airflow channel of the mouthpiece. The aerosol-forming substrate may line the inner wall of the airflow channel.

The aerosol-forming substrate may comprise flavourants. The aerosol-forming substrate may comprise of flavourants. The aerosol-forming substrate may be configured to alter the flavor of the aerosol drawn through the mouthpiece. Due to the aerosol-forming substrate lining the airflow channel, the flavourants may be directly released into the aerosol flowing through the airflow channel.

Preferably, a further aerosol-forming substrate may be used with the aerosol-generating device. The further aerosol-forming substrate may be provided in the main body of the aerosol-generating device for generating an aerosol. The further aerosol-forming substrate may be provided as part of an aerosol-generating article. The aerosol-generating article may be insertable into the aerosol-generating device. The aerosol-generating article may be insertable into the main body of the aerosol-generating device. The aerosol-generating article may be a cartridge. In some embodiments, the aerosol-generating device may comprise means for receiving the aerosol-forming substrate not provided as part of an aerosol-generating article. For example, in some embodiments, the main body may comprise a storage portion such as a liquid storage portion for receiving a liquid aerosol-forming substrate. After aerosol generation in the main body, the generated aerosol is preferably drawn from the main body, through the mouthpiece towards the mouth of a user. In the mouthpiece, the aerosol-forming substrate lining the airflow channel of the mouthpiece may influence one or more properties of the aerosol. The aerosol-forming substrate lining the airflow channel may influence the flavor of the aerosol in a desired way.

The present invention may further relate to a set of mouthpieces, wherein each mouthpiece is configured as described herein and wherein one or more of each mouthpiece comprise an aerosol-forming substrate. The aerosol-forming substrates of the different mouthpieces may be different in flavour (or absence thereof).

The mouthpiece may be configured at least partly insertable into the main body. Configuring the mouthpiece partly insertable into the main body may facilitate engagement of the mouthpiece with the main body. The mouthpiece may be connectable to the main body. The connection between the main body and the mouthpiece may be facilitated by the first connection element of the mouthpiece and the connection portion of the main body. The connection between the mouthpiece and the main body may be configured as a form fit connection.

The part of the mouthpiece being configured insertable into the main body may have a conical shape. The part of the main body receiving the mouthpiece may have a corresponding conical shape. The mouthpiece may have a male conical shape and the main body may have a female conical shape or vice versa. After insertion of the mouthpiece into the main body, the conical part of the mouthpiece inserted into the main body may lie against the conical receiving part of the main body so that a conical joining surface is formed between the conical part of the mouthpiece and the conical part of the main body.

The airflow channel may be arranged inside of the conical portion of the mouthpiece. The airflow channel may be arranged inside of the conical portion of the main body. After the mouthpiece is engaged with the main body, a central airflow channel may be established between the main body and the mouthpiece.

The first connection element may be arranged on an outer surface of the mouthpiece. The first connection element may establish the engagement between the main body and the mouthpiece, when the mouthpiece is engaged with the main body. The first connection element may connect the mouthpiece to the main body. When the mouthpiece is inserted into the main body, the first connection element may contact the main body for establishing the connection between the mouthpiece and the main body. The first connection element may be arranged on the outer wall of the conical part of the mouthpiece that is insertable into the main body. The first connection element may be arranged on the conical joining surface.

The connection portion may be arranged on an inner surface of the main body. The connection portion may facilitate the engagement between the main body and the mouthpiece. The connection portion may facilitate the engagement between the main body and the mouthpiece, when the mouthpiece is engaged with the main body. The connection portion may facilitate attachment between the main body and the mouthpiece. The connection portion may engage the first connection element of the mouthpiece. The connection portion may engage the first connection element of the mouthpiece, when the mouthpiece is inserted into the main body. The connection portion and the first connection element may be engageable. The connection portion may be arranged on the inner surface of the conical portion of the main body which acts as a receiving portion for the mouthpiece. The connection portion may be arranged on the conical joining surface between the main body and the mouthpiece, when the mouthpiece is inserted into the main body.

The connection portion may be configured to facilitate the irreversible change of the first connection element during disengagement of the mouthpiece from the main body. During disengagement of the mouthpiece from the main body, the connection portion may be configured to plastically deform the first connection element. During disengagement of the mouthpiece from the main body, the connection portion may be configured to rupture the first connection element. During disengagement of the mouthpiece from the main body, the connection portion may be configured to shear away the first connection element or parts of the first connection element.

One or both of the first connection element and the connection portion may comprise one or more protrusions or latching lugs. In some embodiments, one or more of the one or more protrusions or latching lugs may extend around the circumference or perimeter of the mouthpiece. For example, a protrusion or latching lug, in some embodiments, may be an annular or substantially annular protrusion or latching lug. A mechanical connection may be facilitated between the first connection element and the connection portion by the protrusions or latching lugs. One or both of the first connection element and the connection portion may comprise one or more recesses for engagement with the protrusions or latching lugs.

The first connection element may be configured as a male connection element and the connection portion may be configured as a female connection element or vice versa.

The first connection element of the mouthpiece may comprise a single connection element. The first connection element of the mouthpiece may comprise more than one connection element. The first connection element may comprise two connection elements. Preferably, the first connection element of the mouthpiece comprises multiple connection elements. The connection portion of the main body may comprise a single connection element. The connection portion of the main body may comprise more than one connection element. The connection portion of the main body may comprise two connection elements. Preferably, the connection portion comprises multiple connection elements. The number of connection elements of the first connection element may be identical to the number of connection elements of the connection portion. Each connection element of the first connection element may be configured to engage a connection element of the connection portion. Each connection element of the first connection element may be configured to be irreversibly changed by the corresponding connection element of the connection portion.

The protrusions or latching lugs may have any desired shape. The protrusions or latching lugs may have an elongate shape. The protrusions or latching lugs may have further connection elements such as hooks. The first connection element may comprise protrusions or latching lugs and the connection portion may comprise recesses or vice versa. The recesses may be configured to engage with the protrusions or latching lugs. The first connection element may comprise protrusions or latching lugs and the connection portion may comprise recesses or vice versa. The protrusions or latching lugs may be configured to engage with the recesses.

The protrusions or latching lugs may have a fin shape. The protrusions or latching lugs may have an elongate shape. The protrusions or latching lugs may be tapered. The protrusions or latching lugs may be tapered at a distal end. The distal end may be opposite a proximal end. The proximal end may be the end that is attached to the mouthpiece. The proximal end may be arranged at the base of the respective protrusion or latching lug. The protrusions or latching lugs may extend perpendicular to the joining surface. The protrusions or latching lugs may be inclined with respect to a perpendicular extension regarding the joining surface. Preferably, the protrusions or latching lugs are inclined in a direction away from the main body. This inclination may facilitate ease of insertion of the mouthpiece into the main body. At the same time, such an inclination may lead to a locking of the protrusions or latching lugs with the connection portion of the main body after insertion of the mouthpiece into the main body. During disengagement, the connection portion may plastically bend the fin shaped protrusions or latching lugs or may shear off the protrusions or latching lugs.

The first connection element and the connection portion may be configured to engage as a snap-fit. A simple and secure connection may be facilitated by the snap-fit. Protrusions or latching lugs together with corresponding recesses may be configured as snap-fit.

The one or more protrusions or latching lugs may each comprise the weakened portion. The weakened portions may be configured to facilitate plastic deformation or fracture of the protrusions or latching lugs. The weakened portion may be configured as an undercut. The undercut may be configured as a portion with less material. The undercut may be configured as a dent. The undercut may be configured as a portion, in which material is removed. The undercut may be arranged adjacent the base of the protrusion or latching lug. Preferably, each protrusion or latching lug comprises at least one undercut. The protrusions or latching lugs may comprise more than one undercut. Each protrusion or latching lug may comprise more than one undercut.

The undercut may be provided on the part of the protrusion or latching lug facing away from the main body, when the mouthpiece is engaged with the main body. In this way, the protrusion or latching lug may be plastically deformed or ruptured away from the main body. Consequently, the mouthpiece can be securely held attached to the main body, when the mouthpiece is inserted into the main body. However, when the mouthpiece is disengaged from the main body, the protrusions or latching lugs will be plastically deformed or sheared off such that the mouthpiece can be disengaged from the main body and re-engagement is no longer possible.

The connection portion of the main body may comprise a resilient ring for engaging with the first connection element of the mouthpiece. The resilient ring may comprise a circular recess on an inner surface of the circular ring. The first connection element of the mouthpiece may be configured to engage with the recess. Preferably, the first connection element may comprise one or more protrusions or latching lugs which may be configured to engage with the recess. The resilient ring may be configured to elastically deform during insertion of the mouthpiece into the main body. Alternatively, the resilient ring may be a rigid. The first connection element may be configured elastic. An elastic first connection element may help to facilitate engagement of the first connection element with the resilient ring. The outer diameter of the first connection element may be larger than the inner diameter of the resilient ring. The first connection element may be configured to be pushed through the aperture of the resilient ring. The first connection element may reach behind the resilient ring to engage the resilient ring. During disengagement of the mouthpiece from the main body, the first connection element of the mouthpiece, preferably the protrusions or latching lugs, may plastically deform or shear off during disengagement of the first connection element from the resilient ring. The recess of the resilient ring may comprise a thread or winding. The first connection portion may engage the resilient ring to enable removing the mouthpiece by a screwing action of the mouthpiece. Disengagement of the mouthpiece from the main body may be facilitated by rotating the mouthpiece.

The resilient ring may be arranged to surround the part of the mouthpiece that is inserted into the main body, when the mouthpiece is inserted into the main body. The resilient ring may be arranged to surround the conical portion of the mouthpiece, once the mouthpiece has been inserted into the main body. The resilient ring may be arranged in a recess of the main body. The resilient ring may be configured as the connection portion of the main body.

The connection portion of the main body may comprise a recess and the first connection element of the mouthpiece may comprise at least two rows of protrusions or latching lugs. In some embodiments, one row of protrusions or latching lugs of the first connection element may be configured for engaging the recess of the connection portion. The recess of the connection portion for engagement with the first row of protrusions or latching lugs may be configured as the resilient ring. The first row of latching lugs may be configured to penetrate through the aperture of the resilient ring during attachment between the mouthpiece and the main body. The first row of latching lugs may be configured elastic. The first row of latching lugs may elastically deform during penetration through the aperture of the resilient ring. The elastic properties of the first row of latching lugs may be aided by each latching lug being provided with the weakened portion, preferably an undercut. The first row of latching lugs may expand behind the resilient ring to anchor the mouthpiece. The second row of protrusions or latching lugs may be configured to further secure the mouthpiece during engagement between the mouthpiece and the main body. The second row of protrusions or latching lugs may act as a second point of contact between the first connection element and the connection portion. The second row of latching lugs may be configured to engage the resilient ring. The second row of latching lugs may be configured to engage the recess of the resilient ring. The second row of latching lugs may be rigid. The second row of latching lugs may not comprise undercuts. The second row of latching lugs may be configured to snap into the recess of the resilient ring during engagement of the mouthpiece with the main body. During rotation of the mouthpiece, the second row of latching lugs may follow the thread or winding of the recess of the resilient ring.

The first connection element may comprise a plurality of micro-recesses and the connection portion may comprise a plurality of micro-protrusions. The first connection element may comprise a plurality of micro-protrusions and the connection portion may comprise a plurality of micro-recesses. The micro-protrusions may be configured to engage the micro-recesses. This configuration of the first connection element and of the connection portion may be configured as a sharkskin configuration. The micro-protrusions may be configured as micro-latching-lugs or micro-snapping-lugs. The micro-recesses may be configured as micro-undercuts. The plurality of micro-protrusions and micro-recesses may facilitate a secure connection between the mouthpiece and the main body.

The main body may have a longitudinal axis. The mouthpiece may have a longitudinal axis. The longitudinal axis of the main body and of the mouthpiece may be identical. After engagement of the mouthpiece with the main body, the mouthpiece and the main body may have a shared longitudinal axis. During engagement of the mouthpiece with the main body, the mouthpiece may be moved along the longitudinal axis. This movement will also be referred to as axial movement. Preferably, the engagement between the first connection element of the mouthpiece and the connection portion of the main body is facilitated during axial movement of the mouthpiece in the direction of the main body.

During disengagement of the mouthpiece from the main body, the mouthpiece may be disengaged along an opposite axial direction. During this opposite axial direction movement, the first connection element of the mouthpiece is irreversibly changed. Preferably, the protrusions or latching lugs of the first connection element are plastically deformed or ruptured by the connection portion of the main body during this movement along the longitudinal axis.

The weakening portion may be configured to plastically deform upon a rotational movement of the mouthpiece relative to the main body, when the first connection element and the connection portion are disengaged. The first connection element may be configured to irreversibly change upon a rotational movement of the mouthpiece relative to the main body, when the first connection element and the connection portion are disengaged. The rotational movement may be facilitated to disengage the mouthpiece from the main body. During the rotational movement, the first connection element may be plastically deformed or ruptured by the connection portion of the main body. Preferably, if the first connection element comprises protrusions or latching lugs, the protrusions or latching lugs will be plastically deformed or ruptured during a rotational movement of the mouthpiece.

The rotational movement may be an alternative to the movement along the longitudinal axis as described above. Alternatively, the axial movement along the longitudinal axis may be combined with a rotational movement. Exemplarily, the axial movement may be configured to attach the mouthpiece with the main body. The rotational movement may be configured to plastically deform the first connection element such as the protrusions or latching lugs of the first connection element or to shear away the first connection element such as the protrusions or latching lugs of the first connection element.

Preferably, the mouthpiece is configured such that engagement of the mouthpiece with the main body can only be facilitated by an axial movement of the mouthpiece towards the main body. Subsequently, a snap fit connection may be established between the first connection element and the connection portion as described herein. For disengagement of the mouthpiece from the main body, the rotational movement may be facilitated. The mouthpiece and the main body may be configured such that the mouthpiece can only be disengaged from the main body by the rotational movement. During the rotational movement, the first connection element, preferably the protrusions or latching lugs of the first connection element, are sheared away by the connection portion of the main body to enable disengagement between the mouthpiece and the main body.

Alternatively, the axial movement may be facilitated for engagement and disengagement or only for disengagement between mouthpiece and main body. Consequently, the rotational movement may alternatively be facilitated for engagement and disengagement or only for engagement between mouthpiece and main body.

The aerosol-generating device may comprise a sealing element. The sealing element may be arranged at the main body. The sealing element may be arranged at the mouthpiece. More than one sealing elements may be provided. The main body as well as the mouthpiece may comprise a sealing element. The sealing element may be configured adjacent the connection portion. The sealing element may be configured to prevent air to escape between the main body and the mouthpiece, when the mouthpiece is engaged with the main body. The sealing element may comprise an O-ring. The sealing element may be arranged in a recess. The sealing elements may be configured surrounding the first connection element of the mouthpiece, when the mouthpiece is engaged with the main body. The sealing element may be arranged at the conical joining surface, when the mouthpiece is engaged with the main body.

The mouthpiece may be configured as a Venturi element. Within the mouthpiece, the airflow channel may be provided. The diameter of the airflow channel of the mouthpiece may gradually increase in a downstream direction. In other words, the diameter of the airflow channel may gradually increase in a direction away from the main body. The diameter of the airflow channel may gradually decrease in an upstream direction. In other words, the diameter of the airflow channel may gradually decrease towards the main body. The mouthpiece may be configured to utilize the Venturi effect. The mouthpiece may have a shape such that the Venturi effect occurs, when fluid flows through the mouthpiece.

The Venturi effect is the reduction of the pressure of a fluid during flow of the fluid through a constricted airflow passage. An upstream portion of the airflow channel near the main body may be configured as the constricted airflow passage.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may be a smoking device that interacts with an aerosol-forming substrate of an aerosol-generating article to generate an aerosol that is directly inhalable into a user's lungs thorough the user's mouth. An aerosol-generating device may be a holder. The device may be an electrically heated smoking device. The aerosol-generating device may comprise a housing, electric circuitry, a power supply, a heating chamber and a heating element.

As used herein with reference to the present invention, the term 'smoking' with reference to a device, article, system, substrate, or otherwise does not refer to conventional smoking in which an aerosol-forming substrate is fully or at least partially combusted. The aerosol-generating device of the present invention is arranged to heat the aerosol-forming substrate to a temperature below a combustion temperature of the aerosol-forming substrate, but at or above a temperature at which one or more volatile compounds of the aerosol-forming substrate are released to form an inhalable aerosol.

The aerosol-generating device, more preferably the main body of the aerosol-generating device, may comprise electric circuitry. The electric circuitry may comprise a microprocessor, which may be a programmable microprocessor. The microprocessor may be part of a controller. The electric circuitry may comprise further electronic components. The electric circuitry may be configured to regulate a supply of power to a heating element. Power may be supplied to the heating element continuously following activation of the aerosol-generating device or may be supplied intermittently, such as on a puff-by-puff basis. The power may be supplied to the heating element in the form of pulses of electrical current. The electric circuitry may be configured to monitor the electrical resistance of the heating element, and preferably to control the supply of power to the heating element dependent on the electrical resistance of the heating element.

The aerosol-generating device, more preferably the main body of the aerosol-generating device, may comprise a power supply, typically a battery. The power supply may be a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery. As an alternative, the power supply may be another form of charge storage device such as a capacitor. The power supply may require recharging and may have a capacity that enables to store enough energy for one or more usage experiences; for example, the power supply may have sufficient capacity to continuously generate aerosol for a period of around six minutes or for a period of a multiple of six minutes. In another example, the power supply may have sufficient capacity to provide a predetermined number of puffs or discrete activations of the heating element.

The aerosol-generating device may comprise a housing. The main body may comprise a housing. A wall of the housing of the aerosol-generating device, preferably a wall of the main body, is provided with at least one air inlet. The air inlet may be configured as a semi-open inlet. The semi-open inlet preferably allows air to enter the aerosol-generating device. Air or liquid may be prevented from leaving the aerosol-generating device through the semi-open inlet. The semi-open inlet may for example be a semi-permeable membrane, permeable in one direction only for air, but is air- and liquid-tight in the opposite direction. The semi-open inlet may for example also be a one-way valve. Preferably, the semi-open inlets allow air to pass through the inlet only if specific conditions are met, for example a minimum depression in the aerosol-generating device or a volume of air passing through the valve or membrane. The air inlet may be fluidly connected with the airflow channel.

The heating element may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum platinum, gold and silver. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese-, gold- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required.

The heating element may be part of the aerosol-generating device, preferably of the main body of the aerosol-generating device. The aerosol-generating device may comprise an internal heating element or an external heating element, or both internal and external heating elements, where "internal" and "external" are with reference to the aerosol-forming substrate. An internal heating element may take any suitable form. For example, an internal heating element may take the form of a heating blade. Alternatively, the internal heater may take the form of a casing or substrate having different electro-conductive portions, or an electrically resistive metallic tube. The internal heating element may comprise a heater substrate. The heater substrate may be covered with one or more layers of glass, preferably on opposite surfaces. This protects the substrate and improves the distribution of heat across the surface of the heater in an active heating area. Electrically conductive tracks such as one or more of silver, gold or platinum tracks may be deposited onto the glass layer. An overlying glass layer may be formed covering the heating element and protecting the heating element from corrosion.

In some embodiments, the internal heating element may be one or more heating needles or rods that run through the center of the aerosol-forming substrate. Other alternatives include a heating wire or filament, for example a Ni—Cr (Nickel-Chromium), platinum, tungsten or alloy wire or a heating plate. Optionally, the internal heating element may be deposited in or on a rigid carrier material. In one such embodiment, the electrically resistive heating element may be formed using a metal having a defined relationship between temperature and resistivity. In such an exemplary device, the metal may be formed as a track on a suitable insulating material, such as ceramic material, and then sandwiched in another insulating material, such as a glass. Heaters formed in this manner may be used to both heat and monitor the temperature of the heating elements during operation.

An external heating element may take any suitable form. For example, an external heating element may take the form of one or more flexible heating foils on a dielectric substrate, such as polyimide. The flexible heating foils can be shaped to conform to the perimeter of the substrate receiving cavity. Alternatively, an external heating element may take the form of a metallic grid or grids, a flexible printed circuit board, a molded interconnect device (MID), ceramic heater, flexible carbon fibre heater or may be formed using a coating technique, such as plasma vapour deposition, on a suitable shaped substrate. An external heating element may also be formed using a metal having a defined relationship between temperature and resistivity. In such an exemplary device, the metal may be formed as a track between two layers of suitable insulating materials. An external heating element formed in this manner may be used to both heat and monitor the temperature of the external heating element during operation.

The internal or external heating element may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. In one embodiment, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy. The heat sink or heat reservoir may be arranged such that it is directly in contact with the aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The heating element advantageously heats the aerosol-forming substrate by means of conduction. The heating element may be at least partially in contact with the substrate, or the carrier on which the substrate is deposited. Alternatively, the heat from either an internal or external heating element may be conducted to the substrate by means of a heat conductive element. As a further alternative, the heating element may be configured as an induction heating element. In this case, the heating element comprises an induction coil and a susceptor. The induction coil receives AC current from the power supply to create an induction field. The induction field is configured to heat the susceptor. The susceptor may be configured surrounding the aerosol-forming substrate as an external heating element or configured to penetrate into the aerosol-forming substrate as an insulating element.

During operation, the aerosol-forming substrate may be completely contained within the aerosol-generating device. In that case, a user may puff on a mouthpiece of the aerosol-generating device.

As used herein, the term 'aerosol-forming substrate' relates to a substrate capable of releasing one or more volatile compounds that can form an aerosol. Such volatile compounds may be released by heating the aerosol-forming substrate. An aerosol-forming substrate may conveniently be part of an aerosol-generating article or smoking article.

The aerosol-forming substrate may be a solid aerosol-forming substrate. The aerosol-forming substrate may comprise both solid and liquid components. The aerosol-forming substrate may be a liquid aerosol-forming substrate. The aerosol-forming substrate may comprise a tobacco-containing material containing volatile tobacco flavour compounds which are released from the substrate upon heating. The aerosol-forming substrate may comprise a non-tobacco material. The aerosol-forming substrate may comprise an aerosol former that facilitates the formation of a dense and stable aerosol. Examples of suitable aerosol formers are glycerine and propylene glycol.

If the aerosol-forming substrate is a solid aerosol-forming substrate, the solid aerosol-forming substrate may comprise, in some embodiments, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise combining one or both of tobacco leaf lamina and tobacco leaf stems. Alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

In some embodiments, the aerosol-forming substrate comprises a gathered crimpled sheet of homogenised tobacco material. As used herein, the term 'crimped sheet' denotes a sheet having a plurality of substantially parallel ridges or corrugations. Preferably, when the aerosol-generating article has been assembled, the substantially parallel ridges or corrugations extend along or parallel to the longitudinal axis of the aerosol-generating article. This advantageously facilitates gathering of the crimped sheet of homogenised tobacco material to form the aerosol-forming substrate. However, it will be appreciated that crimped sheets of homogenised tobacco material for inclusion in the aerosol-generating article may alternatively or in addition have a plurality of substantially parallel ridges or corrugations that are disposed at an acute or obtuse angle to the longitudinal axis of the aerosol-generating article when the aerosol-generating article has been assembled. In certain embodiments, the aerosol-forming substrate may comprise a gathered sheet of homogenised tobacco material that is substantially evenly textured over substantially its entire surface. For example, the aerosol-forming substrate may comprise a gathered crimped sheet of homogenised tobacco material comprising a plurality of substantially parallel ridges or corrugations that are substantially evenly spaced-apart across the width of the sheet.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

The aerosol-forming substrate is a substrate capable of releasing volatile compounds that can form an aerosol. The volatile compounds may be released by heating the aerosol-forming substrate. The aerosol-forming substrate may comprise plant-based material. The aerosol-forming substrate may comprise tobacco. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material. The aerosol-forming substrate may comprise homogenised plant-based material.

The aerosol-forming substrate may comprise at least one aerosol-former. An aerosol-former is any suitable known compound or mixture of compounds that, in use, facilitates formation of a dense and stable aerosol and that is substantially resistant to thermal degradation at the temperature of operation of the system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Aerosol formers may be polyhydric alcohols or mixtures thereof, such as triethylene glycol, 1,3-butanediol and glycerine. The aerosol-former may be propylene glycol. The aerosol former may comprise both glycerine and propylene glycol.

The aerosol-forming substrate may be provided in a liquid form. The liquid aerosol-forming substrate may comprise other additives and ingredients, such as flavourants. The liquid aerosol-forming substrate may comprise water, solvents, ethanol, plant extracts and natural or artificial flavours. The liquid aerosol-forming substrate may comprise nicotine. The liquid aerosol-forming substrate may have a nicotine concentration of between about 0.5% and about 10%, for example about 2%. The liquid aerosol-forming substrate may be contained in a liquid storage portion of the aerosol-generating article, in which case the aerosol-generating article may be denoted as a cartridge.

As used herein, the term 'aerosol-generating article' refers to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable.

The aerosol-generating article may be substantially cylindrical in shape. The aerosol-generating article may be substantially elongate. The aerosol-generating article may have a length and a circumference substantially perpendicular to the length. The aerosol-generating article may be substantially rod shaped. The aerosol-forming substrate may be substantially cylindrical in shape. The aerosol-forming substrate may be substantially elongate. The aerosol-forming substrate may also have a length and a circumference substantially perpendicular to the length. The aerosol-forming substrate may be substantially rod shaped.

Operation of the aerosol-generating device, preferably of the heating element, may be triggered by a puff detection system. Alternatively, the heating element may be triggered by pressing an on-off button, held for the duration of the user's puff. The puff detection system may be provided as a sensor, which may be configured as an airflow sensor to measure the airflow rate. The airflow rate is a parameter characterizing the amount of air that is drawn through the airflow channel of the aerosol-generating device per time by the user. The initiation of the puff may be detected by the airflow sensor when the airflow exceeds a predetermined threshold. Initiation may also be detected upon a user activating a button.

The sensor may be configured as a pressure sensor to measure the pressure of the air inside the aerosol-generating device which is drawn through the airflow channel of the device by the user during a puff. The sensor may be configured to measure a pressure difference or pressure drop between the pressure of ambient air outside of the aerosol-generating device and of the air which is drawn through the device by the user. The pressure of the air may be detected at the air inlet, the mouthpiece of the device, the heating chamber or any other passage or chamber within the aerosol-generating device, through which the air flows. When the user draws on the aerosol-generating device, a negative pressure or vacuum is generated inside the device, wherein the negative pressure may be detected by the pressure sensor. The term "negative pressure" is to be understood as a pressure which is relatively lower than the pressure of ambient air. In other words, when the user draws on the device, the air which is drawn through the device has a pressure which is lower than the pressure off ambient air outside of the device. The initiation of the puff may be detected by the pressure sensor if the pressure difference exceeds a predetermined threshold.

Features described in relation to one embodiment may equally be applied to other embodiments of the invention.

The invention will be further described, by way of example only, with reference to the accompanying drawings in which.

Figure 1:
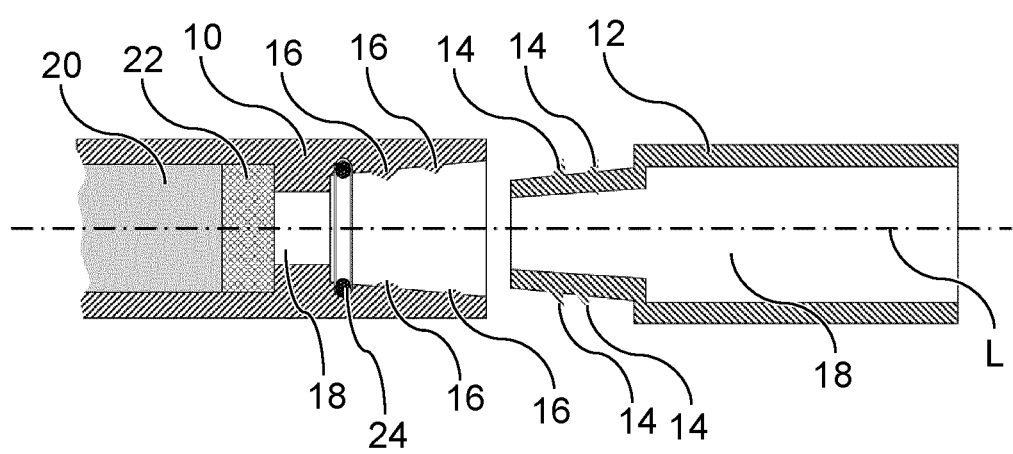
FIG. 1 shows an aerosol-generating device comprising a main body and a removable mouthpiece.

FIG. 1 shows an aerosol-generating device comprising a main body 10 and a removable mouthpiece 12. The mouthpiece 12 and the main body 10 are configured engageable. For facilitating the engagement between the mouthpiece 12 and the main body 10, the mouthpiece 12 comprises a first connection element 14. For facilitating the engagement between the mouthpiece 12 and the main body 10, the main body 10 comprises a connection portion 16. The first connection element 14 is configured engageable with the connection portion 16.

The aerosol-generating device comprises a longitudinal axis L. The main body 10 and the mouthpiece 12 comprise the same longitudinal axis L. The aerosol-generating device comprises an airflow channel 18. The airflow channel 18 is preferably a central airflow channel 18. An aerosol generated in the main body 10 can flow through the airflow channel 18. For generating the aerosol, the main body 10 may comprise aerosol-forming substrate 20. The aerosol-forming substrate 20 may be provided in the form of an aerosol-generating article, a cartridge or in liquid form in a liquid storage portion. In the embodiment shown in FIG. 1, the aerosol-forming substrate 20 is provided in the form of an aerosol-generating article which further comprises a filter 22.

Between the mouthpiece 12 and the main body 10, a sealing element 24 may be provided. The sealing element 24 may be configured as an O-ring. The sealing element 24 may be configured to prevent air from escaping between the mouthpiece 12 and the main body 10, when the mouthpiece 12 is engaged with the main body 10.

The part of the mouthpiece 12 that is inserted into the main body 10 has a conical shape. The part of the main body 10 receiving the mouthpiece 12 has a corresponding conical shape. When the mouthpiece 12 is engaged with the main body 10, a conical joining surface is formed between the main body 10 and the mouthpiece 12.

Figure 2:
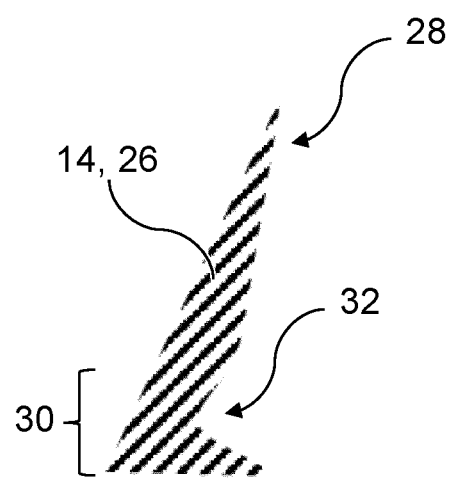
FIG. 2 shows a first connection element of the mouthpiece.

FIG. 2 shows an embodiment of the first connection element 14 of the mouthpiece 12. The first connection element 14 may be configured as a latching lug 26 as depicted in FIG. 2. The latching lug 26 may also be referred to as protrusion. Preferably, the first connection element 14 comprises multiple latching lugs 26. The latching lug 26 may have an elongate shape. The latching lug 26 may have a tapered end 28. The latching lug 26 may have a base 30. The base 30 of the latching lug 26 may be connected to the mouthpiece 12. The tapered end 28 may be arranged opposite the base 30. The tapered end 28 may be configured to engage the connection portion 16 of the main body 10. The latching lug 26 may be inclined away from the main body 10. The latching lug 26 may comprise a weakened region 32 in the form of an undercut. The weakened region 32 may be configured to enable a plastic deformation or a rupture of the latching lug 26 during disengagement of the mouthpiece 12 from the main body 10.

During engagement between the mouthpiece 12 and the main body 10, the mouthpiece 12 may be moved along the longitudinal axis L in the direction of the main body 10. The latching lug 26 may engage the connection portions 16. The connection portions 16 in FIG. 2 comprise protrusions for engaging with the latching lugs 26 of the first connection element 14 of the mouthpiece 12. In other embodiments, the connection portions 16 of the main body 10 may comprise recesses so that the latching lug 26 may engage with the recesses. After the mouthpiece 12 has been inserted into the main body 10, a secure connection may be established between the mouthpiece 12 and the main body 10.

For disengagement of the mouthpiece 12 from the main body 10, a user may apply a rotational movement. During the rotational movement, the engagement between the connection portion 16 of the main body 10 and the first connection element 14 of the mouthpiece 12 may lead to a plastic deformation or rupture of the first connection element 14. Preferably, the latching lugs 26 are plastically deformed in the region of the weakened region 32. For example, the latching lugs 26 may be plastically bent in the weakened region 32. Alternatively, the latching lugs 26 are sheared off at the weakened region 32.

Alternative to the movement along the longitudinal axis L during engagement and the rotational movement during disengagement, one or both of the movement along the longitudinal axis L and the rotational movement around the longitudinal axis L may be utilized for one or both of the engagement and disengagement of mouthpiece 12 and main body 10.

Figure 3:
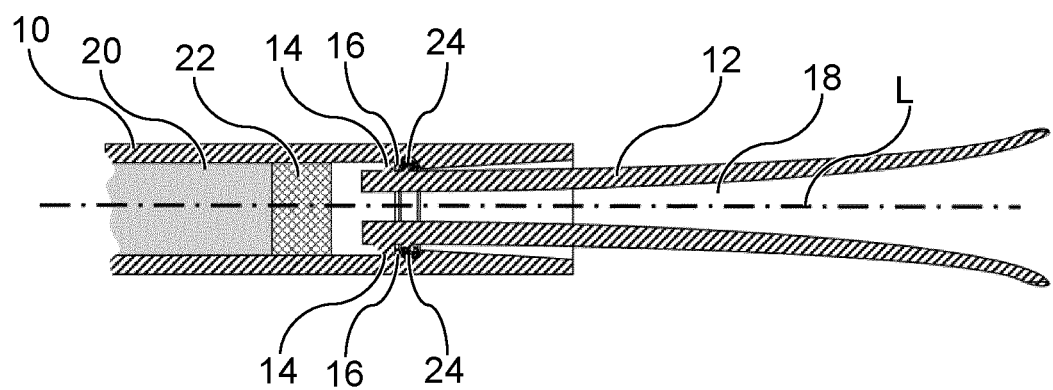
FIG. 3 shows the main body and the removable mouthpiece in an engaged state.

FIG. 3 shows an embodiment of the aerosol-generating device in which the mouthpiece 12 and the main body 10 are engaged. The first connection element 14 and the connection portion 16 are configured as a snap-fit connection. Furthermore, the sealing element 24 arranged between the main body 10 and the mouthpiece 12 is depicted in FIG. 3 so as to prevent air from leaking between the mouthpiece 12 and the main body 10.

The mouthpiece 12 may be configured as a Venturi element. As depicted in FIG. 3, the diameter of the airflow channel 18 of the mouthpiece 12 may gradually increase in a downstream direction. In other words, the diameter of the airflow channel 18 may gradually increase in a direction away from the main body 10. The mouthpiece 12 may be configured as a flared mouthpiece 12. The diameter of the airflow channel 18 may gradually decrease towards the main body 10. The mouthpiece 12 may be configured to utilize the Venturi effect. The mouthpiece 12 may have a shape such that the Venturi effect occurs, when fluid flows through the mouthpiece 12.

The Venturi effect is the reduction of the pressure of a fluid during flow of the fluid through a constricted airflow passage. An upstream portion of the airflow channel 18 near the main body 10 may be configured as the constricted airflow passage. Air comprising vaporized aerosol-forming substrate may flow through the constricted portion of the airflow channel 18 of the mouthpiece 12. After exiting the constricted portion of the airflow channel 18, the air may expand and cool down. The cooling of the air may lead to droplet formation and therefore aerosol generation.

Figure 4:
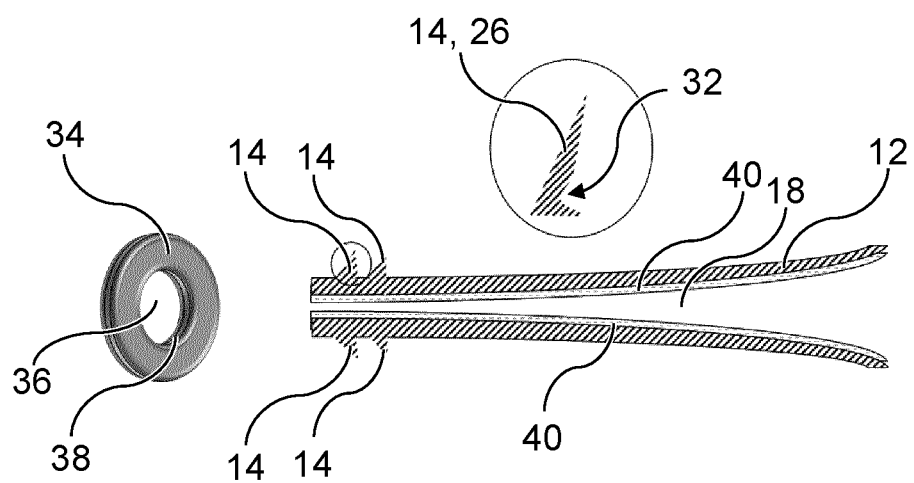
FIG. 4 shows an embodiment of a connection portion of the main body and the first connection element.

FIG. 4 shows an embodiment, in which the connection portion 16 of the main body 10 comprises a resilient ring 34. The first connection element 14 may engage the resilient ring 34 to facilitate a secure connection between the mouthpiece 12 and the main body 10. The first connection element 14 may comprise a first row of latching lugs 26 and a second row of latching lugs 26 as depicted in FIG. 4. The first row of latching lugs 26 may be configured to engage the resilient ring 34. In more detail, the first row of latching lugs 26 may be configured to penetrate through the aperture of the resilient ring 34 during attachment between the mouthpiece 12 and the main body 10. During penetration, the first row of latching lugs 26 may be pushed through an inner opening 36 of the resilient ring 34. For facilitating this penetration action, the first row of latching lugs 26 may comprise undercuts 32. Due to these undercuts 32, the first row of latching lugs 26 may have a degree of flexibility. The outer diameter of the first row of latching lugs 26 may be larger than the inner diameter of the resilient ring 34. Due to the flexibility of the first row of latching lugs 26 by means of the undercuts 32, the first row of latching lugs 26 may be configured to be pushed through the inner opening 36 of the resilient ring 34. After being pushed through the inner opening 36 of the resilient ring 34, the first row of latching lugs 26 may reach behind the resilient ring 34 to prevent retraction of the mouthpiece 12. Consequently, the first row of latching lugs 26 may engage the resilient ring 34 after penetration of the resilient ring 34. The flexibility of the first row of latching lugs 26 may result in an expansion of the first row of latching lugs 26 after being pushed through the resilient ring 34. After penetration of the inner opening 36 of the resilient ring 34, the first row of latching lugs 26 may facilitate axial fixation of the mouthpiece 12 with respect to the main body 10.

The second row of latching lugs 26 may be configured to further aid securely connecting the mouthpiece 12 with the main body 10. The second row of latching lugs 26 may be configured to engage a circumferential recess 38 of the resilient ring 34. The circumferential recess 38 of the resilient ring 34 may be arranged at the inner surface of the inner opening 36 of the resilient ring 34. The second row of latching lugs 26 may preferably not be provided with undercuts 32. In this way, structural integrity of the second row of latching lugs 26 may be secured during a disengagement action of the mouthpiece 12 and the main body 10. The circumferential recess 38 of the resilient ring 34 may be configured as a thread or winding. Engagement between the second row of latching lugs 26 and the thread shaped circumferential recess 38 of the resilient ring 34 may enable rotation of the mouthpiece 12 with respect to the main body 10. Engagement between the second row of latching lugs 26 and the circumferential recess 38 of the resilient ring 34 may be facilitated after the first row of latching lugs 26 has been pushed through the inner opening 36 of the resilient ring 34. The engagement between the second row of latching lugs 26 and the circumferential recess 38 may be a snap fit.

Particularly, disengagement of the mouthpiece 12 from the main body 10 may be facilitated by rotating the mouthpiece 12. During rotation of the mouthpiece 12, the second row of latching lugs 26 engaged with the circumferential recess 38 of the resilient ring 34 may follow the thread shape of the circumferential recess 38. The circumferential recess 38 may be configured such that the mouthpiece 12 is removed from the main body 10 during rotation of the mouthpiece 12 relative to the main body 10. The mouthpiece 12 may be removed from the main body 10 by a screwing action. During rotation of the mouthpiece 12, the first row of latching lugs 26 is preferably bend or sheared off at the undercuts 32. The shearing off of the first row of latching lugs 26 enables disengagement of the mouthpiece 12 and the main body 10. At the same time, shearing off of the first row of latching lugs 26 prevents re-engagement of the mouthpiece 12 and the main body 10.

FIG. 4 further shows that the inner surface of the airflow channel 18 of the mouthpiece 12 is lined with a layer 40 of aerosol-forming substrate. The airflow channel 18 of the mouthpiece 12 may be fully or partially lined with the layer 40 of aerosol-forming substrate. The layer 40 of aerosol-forming substrate may comprise, preferably consist of, flavourants. The layer 40 of aerosol-forming substrate may be configured to influence one or more properties, preferably the flavor, of the aerosol flowing through the airflow channel 18. After depletion of the layer 40 of aerosol-forming substrate, a user may remove the mouthpiece 12 from the main body 10. The irreversible change of the first row of latching lugs 26 during disengagement of the mouthpiece 12 and the main body 10 prevents re-engagement of the mouthpiece 12 and the main body 10 with a depleted layer 40 of aerosol-forming substrate.

The invention claimed is:

1. An aerosol-generating device for generating an inhalable vapor comprising:
   a main body comprising a connection portion; wherein the main body is configured to receive or contains an aerosol-forming substrate,
   a removable mouthpiece comprising a first connection element,
   wherein the first connection element is configured removably engageable with the connection portion of the main body,
   wherein the first connection element is configured to irreversibly change upon disengagement of the first connection element from the connection portion of the main body, wherein the first connection element comprises a weakened region configured to plastically deform or to fracture during disengagement of the first connection element from the connection portion of the main body, wherein the connection portion of the main body remains intact for engagement with a new mouthpiece, wherein the weakened region is configured as an undercut.

2. The aerosol-generating device according to claim 1, wherein the weakened region is configured to plastically deform upon a rotational movement of the mouthpiece relative to the main body, when the first connection element and the connection portion are engaged.

3. The aerosol-generating device according to claim 1, wherein the weakened region is configured to prevent re-engagement between the first connection element and the connection portion of the main body, to connect the mouthpiece to the main body after disengagement of the first connection element of the mouthpiece from the connection portion of the main body.

4. The aerosol-generating device according to claim 1, wherein the first connection element is configured as a single use connection element.

5. The aerosol-generating device according to claim 1, wherein the mouthpiece comprises an airflow channel and an aerosol-forming substrate at least partially lining a surface of the airflow channel.

6. The aerosol-generating device according to claim 1, wherein the mouthpiece is configured at least partly insertable into the main body.

7. The aerosol-generating device according to claim 1, wherein the first connection element is arranged on an outer surface of the mouthpiece.

8. The aerosol-generating device according to claim 1, wherein the connection portion is arranged on an inner surface of the main body.

9. The aerosol-generating device according to claim 1, wherein one or both of the first connection element and the connection portion comprises one or more protrusion or latching lugs.

10. The aerosol-generating device according to claim 1, wherein the first connection element and the connection portion are configured to engage as a snap-fit.

11. The aerosol-generating device according to claim 1, wherein the connection portion of the main body comprises a resilient ring for engaging with the first connection element of the mouthpiece.

12. The aerosol-generating device according to claim 1, wherein the connection portion of the main body comprises a recess and the first connection element of the mouthpiece comprises at least two rows of protrusions, wherein one row of protrusions of the first connection element is configured for engaging the recess of the connection portion.

13. The aerosol-generating device according to claim 1, wherein the first connection element comprises a plurality of micro-protrusions and the connection portion comprises a plurality of micro-recesses.

* * * * *